(12) United States Patent
Esslinger et al.

(10) Patent No.: US 8,519,106 B2
(45) Date of Patent: Aug. 27, 2013

(54) MONOCLONAL HUMAN TUMOR-SPECIFIC ANTIBODY

(75) Inventors: Christoph Esslinger, Zürich (CH); Sandra Künzle, Zürich (CH); Irene Abela, Ennetbaden (CH); Alfred Zippelius, Basel (CH); Dirk Jäger, Heidelberg (DE); Alexander Knuth, Zürich (CH); Roger Nitsch, Zumikon (CH); Holger Moch, Zürich (CH); Norbert Göbels, Düsseldorf (CH)

(73) Assignee: University of Zurich, Zurich (CH)

( * ) Notice: Subject to any disclaimer, the term of this patent is extended or adjusted under 35 U.S.C. 154(b) by 286 days.

(21) Appl. No.: 12/530,764

(22) PCT Filed: Mar. 13, 2008

(86) PCT No.: PCT/EP2008/002021
§ 371 (c)(1),
(2), (4) Date: Aug. 11, 2010

(87) PCT Pub. No.: WO2008/110372
PCT Pub. Date: Sep. 18, 2008

(65) Prior Publication Data
US 2010/0330075 A1 Dec. 30, 2010

(30) Foreign Application Priority Data

Mar. 13, 2007 (EP) ..................... 07005180

(51) Int. Cl.
*C12P 21/08* (2006.01)
(52) U.S. Cl.
USPC .................... 530/387.3; 530/391.3
(58) Field of Classification Search
None
See application file for complete search history.

(56) References Cited

U.S. PATENT DOCUMENTS

| | | | |
|---|---|---|---|
| 6,252,052 B1 | 6/2001 | Stockert | |
| 6,338,947 B1 | 1/2002 | Sahin et al. | |
| 7,223,393 B2 * | 5/2007 | Landolfi et al. | 424/133.1 |
| 2003/0236209 A1 * | 12/2003 | Foy et al. | 514/44 |
| 2005/0142620 A1 | 6/2005 | Bangur | |
| 2006/0235207 A1 | 10/2006 | Tsuchiya | |
| 2009/0243296 A1 | 10/2009 | Letas | |

FOREIGN PATENT DOCUMENTS

| | | |
|---|---|---|
| EP | 0 239 400 | 9/1987 |
| EP | 0 451 216 | 10/1991 |
| EP | 0 549 581 | 7/1993 |
| WO | WO 89/09622 | 10/1989 |
| WO | WO 90/07861 | 7/1990 |
| WO | WO 91/10741 | 7/1991 |
| WO | WO 92/05274 | 4/1992 |
| WO | WO 94/02602 | 2/1994 |
| WO | WO 94/04686 | 3/1994 |
| WO | WO 96/33735 | 10/1996 |
| WO | WO 96/34096 | 10/1996 |
| WO | WO 88/09344 | 12/1998 |
| WO | WO 00/20460 | 4/2000 |
| WO | WO 00/30680 | 6/2000 |
| WO | WO 01/07917 | 2/2001 |
| WO | WO 03/086175 | 10/2003 |
| WO | WO 2005/000870 | 1/2005 |
| WO | WO 2005/105139 | 11/2005 |
| WO | WO 2005/116645 | 12/2005 |
| WO | PCT/EP2008/000053 | 7/2008 |
| WO | WO 2008/081008 | 7/2008 |
| WO | PCT/EP2007/005180 | 10/2009 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
Cellular and Molecular Immunology (Eds. Abass et al.; 1991; W.B. Saunders: Philadelphia; p. 54).*
Gnjatic et al., Proceedings of the National Academy of Science, USA, pp. 8862-8867 (2003).
Jager and Knuth, Breast 14, pp. 631-635 (2005).
Russian Patent Office "Office Action" in related U.S. Appl. No. 12/530,764, dated Dec. 16, 2011, 7 pages.
РОЙТ А. и др Иммунология. М. Мир, , 2000, pp. 110-111, 151-152.
Woelbing, et al., 2006, "Uptake of Leishmania major by dendritic cells is mediated by Fcγ receptors and facilitates acquisition of protective immunity" *JEM*, vol. 203, (1), pp. 177-188.
Wardemann, et al., 2003 "Predominant Autoantibody Production by Early Human B Cell Precursors", *Science*, vol. 301, pp. 1374-1377.
Traggiai, et al., 2004, "An efficient method to make human monoclonal antibodies from memory B cells: potent neutralization of SARS coronas", *Nature Medicine*, vol. 10, (8), pp. 871-875.
Stevenson, 2005, "Update on cancer vaccines", *Curr Opin Oncol 17*, pp. 573-577.
Schultz-Thater, et al., 2000, "NY-ESO-1 tumour associated antigen is a cytoplasmic protein detectable by specific monoclonal antibodies in cell lines and clinical specimens" *British Journal of Cancer*, 83(2), pp. 204-208.
Schluesener, et al., 1987, "A monoclonal antibody against a myelin ligodendrocyte glycoprotein induces relapses and demyelination in central nervous system autoimmune disease", *The Journal of Immunology*, vol. 139,(12) pp. 4016-4021.
Sahin, et al., 1995, "Human Neoplasms Elicit Multiple Specific Immune Responses in the Autologous Host", *Proc. Natl. Acad. Sci. USA*, vol. 92, pp. 11810-11813.

(Continued)

*Primary Examiner* — Brad Duffy
(74) *Attorney, Agent, or Firm* — David Wright Tremaine LLP; Sheila R. Gibson; Wenhua Yu

(57) ABSTRACT

Provided are novel human tumor-specific antibodies as well as fragments, derivatives and variants thereof that recognize tumor-associated antigen NY-ESO-1. In addition, pharmaceutical compositions comprising such antibodies and mimics thereof in the treatment of tumors are described.

14 Claims, 4 Drawing Sheets

(56) References Cited

OTHER PUBLICATIONS

Preiss, et al., 2005, "Tumor-induced antibodies resemble the response to tissue damage", *Int. J. Cancer*, 115, pp. 456-462.

Owens, et al., 2003, "Single-Cell Repertoire Analysis Demonstrates that Clonal Expansion Is a Prominent Feature of the B Cell Response in Multiple Sclerosis Cerebrospinal Fluid", *The Journal of Immunology*, 171, pp. 2725-2733.

Küppers, 2003, "B Cells Under Influence: Transformation Of B Cells by Epstein—Barr Virus", *Nature Reviews Immunology*, vol. 3, pp. 801-812.

Jäger, et al.,1998, "Simultaneous Humoral and Cellular Immune Response against Cancer—Testis Antigen NY-ESO-1:Defmition of Human Histocompatibility Leukocyte Antigen (HLA)-A2—binding Peptide Epitopes" *J. Exp. Med*, vol. 187(2), pp. 265-270.

Jäger, et al.,1999, "Humoral Immune Responses Of Cancer Patients Against "Cancer-Testis" Antigen Ny-Eso-1: Correlation With Clinical Events", *Int. J. Cancer (Pred. Oncol.)* 84, pp. 506-510.

Hartmann, et al., 2000, "Mechanism and Function of a Newly Identified CpG DNA Motif in Human Primary B Cells", *Journal of Immunology*, 164, pp. 944-952.

Harris, 2004, "Monoclonal antibodies as therapeutic agents for cancer", *The Lancet Oncol 5*, pp. 292-302.

Davis, et al., 2004, "Recombinant NY-ESO-1 protein with ISCOMATRIX adjuvant induces broad integrated antibody and CD4+ and CD8+ T cell responses in humans", *PNAS*, vol. 101(29), pp. 10697-10702.

Chen, et al., 1998, "Identification of multiple cancerytestis antigens by allogeneic antibody screening of a melanoma cell line library", *Proc. Natl. Acad. Sci. USA*, vol. 95, pp. 6919-6923.

Barbas et al., 2001, "Phage display: A laboratory manual" *Cold Spring Harbor Laboratory Press ISBN 978-087969740-2*.

European Patent Office, European Search Report issued in corresponding European patent application No. 12151047.3, 8 pages.

Gnjatic, et al., "NY-ESO-1: Review of an Immunogenic Tumor Antigen," Advances in Cancer Research, Jan. 1, 2006, pp. 1-30.

Held, et al., "A high-affinity antibody binding the specificity of T-cell receptor to a MHC-class I displayed epitope of the tumor-specific antigen NY-ESO-1," Proceedings Of The Annual Meeting Of The American Association For Cancer Research, Jul. 1, 2003, pp. 1156-1157, vol. 44.

Jäger, et al., "Monitoring CDB T cell responses to NY-ESO-1: Correlation of humoral and cellular immune responses," Proceedings Of The National Academy Of Sciences Of The United States Of America, Apr. 25, 2000, pp. 4760-4765, vol. 97. No. 9.

Kawabata, et al., "Antibody response against NY-ESO-1 in CHP-NY-ESO-1 vaccinated patients," International Journal of Cancer, Feb. 2, 2007, pp. 2178-2184, vol. 120, No. 10.

Stockert, et al., "A Survey of the Humoral Immune Response Of Cancer Patients to a Panel of Human Tumor Antigens," Journal of Experimental Medicine, Apr. 20, 1998, vo.. 187, No. 8.

Tureci, et al., "Humoral Immune Responses of Lung Cancer Patients Against Tumor Antigen NY-ESO-1," Cancer Letters, May 8, 2006, pp. 64-71, vol. 236, No. 1.

Valmori, et al., "Identification of B cell epitopes recognized by antibodies specific for the tumor antigen NY-ESO-1 in cancer patients with spontaneous immune responses," Clinical Immunology, Oct. 1, 2005, vol. 117, No. 1.

Wang, et al., "Human Immunoglobin Variable Region Gene Analysis by Single Cell RT-PCR," Journal of Immunological Methods, Oct. 20, 2000, pp. 217-225, vol. 244, No. 1-2.

Zeng, et al. "Dominant B cell epitope from NY-ESO-1 recognized by sera from a wide spectrum of cancer patients: Implications as a potential biomarker," International Journal of Cancer, Mar. 20, 2005, pp. 268-273, vol. 114, No. 2.

Notice of Reason for Rejection, mailed in related Japanese Patent Application, dated Nov. 6, 2012.

Office Action, mailed in corresponding Chinese Application No. 2008800082682 on Mar. 18, 2013, 1 page.

Office Action, mailed in corresponding Mexican Application No. MX/a/2009/009926 on May 27, 2013, 2 pages.

\* cited by examiner

12D7 VH chain

```
FR1----------------------------CDR1-FR2----------CDR2------
QVQLVQSGGGVVRPGGSLRLSCAASGFSFIDYGMSWVRQVPGKGLEWVAGMNWSGDKKG
-------FR3---------------------------CDR3-----JH---------
HAESVKGRFIISRDNAKNTLYLEMSSLRVEDTALYFCARGEYSNRFDPRGRGTLVTVSS
```

```
CAGGTGCAGCTGGTGCAGTCTGGGGGAGGCGTGGTACGGCCTGGGGGGTCCCTGAGACTCTC
CTGTGCAGCCTCTGGATTCAGCTTTATTGATTATGGCATGAGTTGGGTCCGCCAAGTTCCAG
GGAAGGGGCTGGAGTGGGTCGCTGGCATGAATTGGAGCGGCGATAAAAAAGGTCATGCGGAG
TCTGTGAAGGGCCGATTCATCATTTCCAGAGACAACGCCAAGAACACCCTGTATCTAGAAAT
GAGCAGCCTAAGAGTCGAAGACACGGCCCTGTATTTTTGTGCGAGAGGGGAGTATAGCAATC
GGTTCGACCCCCGGGGCCGGGGAACCCTGGTCACCGTCTCCTCA
```

12D7 VkL chain

```
FR1--------------------CDR1------------FR2------------CDR2-
DIVMTQTPLSLPVTLGQPASLSCRSSQSLVFTDGNTYLNWFQQRPGQSPRRLIYKVSSR
--FR3---------------------------CDR3-----JK--------
DPGVPDRFSGTGSGTDFTLEISRVEAEDIGVYYCMQGTHWPPIFGQGTKVEIK
```

```
GATATTGTGATGACCCAGACTCCACTCTCCCTGCCCGTCACCCTTGGACAGCCGGCCTCCCT
CTCCTGCAGGTCTAGTCAAAGCCTCGTATTCACTGATGGAAACACCTACTTGAATTGGTTTC
AGCAGAGGCCAGGCCAATCTCCACGGCGCCTAATTTATAAGGTCTCTTCTCGTGACCCTGGT
GTCCCCGACAGATTCAGCGGCACTGGGTCAGGCACTGATTTCACACTGGAAATCAGCAGGGT
GGAGGCTGAGGATATTGGGGTTTACTACTGCATGCAAGGGACGCACTGGCCTCCGATTTTTG
GCCAGGGGACCAAGGTGGAGATCAAA
```

Fig. 4

SEQUENCE LISTING

```
<160> NUMBER OF SEQ ID NOS: 11

<210> SEQ ID NO 1
<211> LENGTH: 354
<212> TYPE: DNA
<213> ORGANISM: Homo sapiens
<220> FEATURE:
<221> NAME/KEY: V_region
<222> LOCATION: (1)..(354)
<223> OTHER INFORMATION: 12D7-variable heavy (Vh) chain sequence
<220> FEATURE:
<221> NAME/KEY: CDS
<222> LOCATION: (1)..(354)

<400> SEQUENCE: 1 cag gtg cag ctg gtg cag tct ggg gga ggc gtg gta cgg cct ggg ggg      48
Gln Val Gln Leu Val Gln Ser Gly Gly Gly Val Val Arg Pro Gly Gly
1               5                   10                  15 tcc ctg aga ctc tcc tgt gca gcc tct gga ttc agc ttt att gat tat      96
Ser Leu Arg Leu Ser Cys Ala Ala Ser Gly Phe Ser Phe Ile Asp Tyr
            20                  25                  30 ggc atg agt tgg gtc cgc caa gtt cca ggg aag ggg ctg gag tgg gtc     144
Gly Met Ser Trp Val Arg Gln Val Pro Gly Lys Gly Leu Glu Trp Val
        35                  40                  45 gct ggc atg aat tgg agc ggc gat aaa aaa ggt cat gcg gag tct gtg     192
Ala Gly Met Asn Trp Ser Gly Asp Lys Lys Gly His Ala Glu Ser Val
    50                  55                  60 aag ggc cga ttc atc att tcc aga gac aac gcc aag aac acc ctg tat     240
Lys Gly Arg Phe Ile Ile Ser Arg Asp Asn Ala Lys Asn Thr Leu Tyr
65                  70                  75                  80 cta gaa atg agc agc cta aga gtc gaa gac acg gcc ctg tat ttt tgt     288
Leu Glu Met Ser Ser Leu Arg Val Glu Asp Thr Ala Leu Tyr Phe Cys
                85                  90                  95 gcg aga ggg gag tat agc aat cgg ttc gac ccc cgg ggc cgg gga acc     336
Ala Arg Gly Glu Tyr Ser Asn Arg Phe Asp Pro Arg Gly Arg Gly Thr
            100                 105                 110 ctg gtc acc gtc tcc tca                                             354
Leu Val Thr Val Ser Ser
        115

<210> SEQ ID NO 2
<211> LENGTH: 118
<212> TYPE: PRT
<213> ORGANISM: Homo sapiens
```

-continued

<400> SEQUENCE: 2

| Gln | Val | Gln | Leu | Val | Gln | Ser | Gly | Gly | Val | Val | Arg | Pro | Gly | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Leu | Arg | Leu | Ser | Cys | Ala | Ala | Ser | Gly | Phe | Ser | Phe | Ile | Asp | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Met | Ser | Trp | Val | Arg | Gln | Val | Pro | Gly | Lys | Gly | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Gly | Met | Asn | Trp | Ser | Gly | Asp | Lys | Lys | Gly | His | Ala | Glu | Ser | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Gly | Arg | Phe | Ile | Ile | Ser | Arg | Asp | Asn | Ala | Lys | Asn | Thr | Leu | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Glu | Met | Ser | Ser | Leu | Arg | Val | Glu | Asp | Thr | Ala | Leu | Tyr | Phe | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Gly | Glu | Tyr | Ser | Asn | Arg | Phe | Asp | Pro | Arg | Gly | Arg | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Val | Thr | Val | Ser | Ser |
|-----|-----|-----|-----|-----|-----|
|     |     |     |     | 115 |     |

<210> SEQ ID NO 3
<211> LENGTH: 336
<212> TYPE: DNA
<213> ORGANISM: Homo sapiens
<220> FEATURE:
<221> NAME/KEY: V_region
<222> LOCATION: (1)..(336)
<223> OTHER INFORMATION: 12D7-variable kappa light (Vkappa) chain
      sequence
<220> FEATURE:
<221> NAME/KEY: CDS
<222> LOCATION: (1)..(336)

<400> SEQUENCE: 3

```
gat att gtg atg acc cag act cca ctc tcc ctg ccc gtc acc ctt gga      48
Asp Ile Val Met Thr Gln Thr Pro Leu Ser Leu Pro Val Thr Leu Gly
1               5                   10                  15 cag ccg gcc tcc ctc tcc tgc agg tct agt caa agc ctc gta ttc act      96
Gln Pro Ala Ser Leu Ser Cys Arg Ser Ser Gln Ser Leu Val Phe Thr
            20                  25                  30 gat gga aac acc tac ttg aat tgg ttt cag cag agg cca ggc caa tct     144
Asp Gly Asn Thr Tyr Leu Asn Trp Phe Gln Gln Arg Pro Gly Gln Ser
        35                  40                  45 cca cgg cgc cta att tat aag gtc tct tct cgt gac cct ggt gtc ccc     192
Pro Arg Arg Leu Ile Tyr Lys Val Ser Ser Arg Asp Pro Gly Val Pro
    50                  55                  60 gac aga ttc agc ggc act ggg tca ggc act gat ttc aca ctg gaa atc     240
Asp Arg Phe Ser Gly Thr Gly Ser Gly Thr Asp Phe Thr Leu Glu Ile
65                  70                  75                  80 agc agg gtg gag gct gag gat att ggg gtt tac tac tgc atg caa ggg     288
Ser Arg Val Glu Ala Glu Asp Ile Gly Val Tyr Tyr Cys Met Gln Gly
                85                  90                  95 acg cac tgg cct ccg att ttt ggc cag ggg acc aag gtg gag atc aaa     336
Thr His Trp Pro Pro Ile Phe Gly Gln Gly Thr Lys Val Glu Ile Lys
            100                 105                 110
```

<210> SEQ ID NO 4
<211> LENGTH: 112
<212> TYPE: PRT
<213> ORGANISM: Homo sapiens

<400> SEQUENCE: 4

| Asp | Ile | Val | Met | Thr | Gln | Thr | Pro | Leu | Ser | Leu | Pro | Val | Thr | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Gln Pro Ala Ser Leu Ser Cys Arg Ser Ser Gln Ser Leu Val Phe Thr
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Ser Arg Asp Pro Gly Val Pro
     50                  55                  60

Asp Arg Phe Ser Gly Thr Gly Ser Gly Thr Asp Phe Thr Leu Glu Ile
 65                  70                  75                  80

Ser Arg Val Glu Ala Glu Asp Ile Gly Val Tyr Tyr Cys Met Gln Gly
                 85                  90                  95

Thr His Trp Pro Pro Ile Phe Gly Gln Gly Thr Lys Val Glu Ile Lys
             100                 105                 110
```

<210> SEQ ID NO 5
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Denomination of CDR protein sequences in Kabat
      Nomenclature of 12D7 Vh, CDR1

<400> SEQUENCE: 5

```
Asp Tyr Gly Met Ser
1               5
```

<210> SEQ ID NO 6
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Denomination of CDR protein sequences in Kabat
      Nomenclature of 12D7 Vh, CDR2

<400> SEQUENCE: 6

```
Gly Met Asn Trp Ser Gly Asp Lys Lys Gly His Ala Glu Ser Val Lys
1               5                   10                  15

Gly
```

<210> SEQ ID NO 7
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Denomination of CDR protein sequences in Kabat
      Nomenclature of
      12D7 Vh, CDR1

<400> SEQUENCE: 7

```
Gly Glu Tyr Ser Asn Arg Phe Asp Pro
1               5
```

<210> SEQ ID NO 8
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: Denomination of CDR protein sequences in Kabat
      Nomenclature of 12D7 Vkappa, CDR1

```
<400> SEQUENCE: 8

Arg Ser Ser Gln Ser Leu Val Phe Thr Asp Gly Asn Thr Tyr Leu Asn
1               5                   10                  15

<210> SEQ ID NO 9
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Denomination of CDR protein sequences in Kabat
      Nomenclature of 12D7 Vkappa, CDR2

<400> SEQUENCE: 9

Lys Val Ser Ser Arg Asp Pro
1               5

<210> SEQ ID NO 10
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Denomination of CDR protein sequences in Kabat
      Nomenclature of 12D7 Vkappa, CDR3

<400> SEQUENCE: 10

Met Gln Gly Thr His Trp Pro Pro Ile
1               5

<210> SEQ ID NO 11
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: Peptide derived from NY-ESO-1 protein,
      corresponding to amino acid residues 11 to 30 of the mature NY-
      ESO-1 protein; see for example UniProtKB/Swiss-Prot entry under
      primary accession number P78358

<400> SEQUENCE: 11

Ser Thr Gly Asp Ala Asp Gly Pro Gly Gly Pro Gly Ile Pro Asp Gly
1               5                   10                  15

Pro Gly Gly Asn
            20
```

MONOCLONAL HUMAN TUMOR-SPECIFIC ANTIBODY

FIELD OF THE INVENTION

The present invention generally relates to novel tumor-specific binding molecules, particularly human antibodies as well as fragments, derivatives and variants thereof that recognize tumor antigens and tumor-associated antigens, respectively. In addition, the present invention relates to pharmaceutical compositions comprising such binding molecules, antibodies and mimics thereof in the treatment of various tumors, in particular melanoma, breast cancer and metastasis.

BACKGROUND OF THE INVENTION

Humoral immune responses to tumors occur in a relatively high frequency in (1, 2). This phenomenon was exploited to identify a variety of tumor-associated antigens (taa) by screening autologous expression libraries with serum from cancer patients (1). Several of these taa now serve as T cell antigens for the induction of anti-tumor CTL-responses in patients (3, 4). This preference for the cellular-, in most cases cytotoxic immune response as therapeutic strategy is now being reconsidered and novel vaccines are designed to also induce antibody responses. In part, this change of concept may have been influenced by the recent success of various monoclonal antibodies for tumor therapy such as trastuzumab (Herceptin) and bevacizumab (Avastin) (5). While these monoclonal antibodies had been specifically raised against targets of presumed oncological relevance, antibodies occurring in cancer patients, either spontaneously or upon vaccination form a different class of molecules the therapeutic significance of which had been difficult to assess. This is mostly due to the lack of straightforward experimental approaches for their isolation and subsequent characterization in vitro and in animal models of human cancer.

Thus, there is a need to overcome the above-described limitations and to provide a therapeutic and diagnostic antibody against antigens involved in cancer.

SUMMARY OF THE INVENTION

The present invention makes use of the tumor-specific immune response of cancer patients for the isolation of tumor antigen and tumor-associated antigen (taa) specific human monoclonal antibodies. In particular, experiments performed in accordance with the present invention were successful in the isolation of a monoclonal antibody specific for the taa NY-ESO-1 from a melanoma patient who showed a serum titer to NY-ESO-1 and a partial clinical response. For isolating the human antibody specific for a tumor antigen and taa, respectively, immunohistochemistry (IHC) using tissue microarrays (TMA) were used.

The present invention is thus directed to human antibodies, antigen-binding fragments and similar antigen binding molecules which are capable of recognizing tumor-associated antigen NY-ESO-1. Furthermore, the present invention relates to compositions comprising said antibodies and to immunotherapeutic and immunodiagnostic methods using the same.

In a particularly preferred embodiment of the present invention, the human antibody or antigen-binding fragment thereof demonstrates the immunological binding characteristics of an antibody characterized by the variable regions $V_H$ and/or $V_L$ as set forth in FIG. 4 (SEQ ID NOs: 2 and 4).

Alternatively, the antibody is a humanized, xenogeneic, or a chimeric human-murine antibody, the latter being particularly useful for diagnostic methods and studies in animals. Therapeutic compositions including the antibody or active fragments thereof, or agonists and cognate molecules, or alternately, antagonists of the same, and methods of use of such compositions in the prevention, diagnosis or treatment of a tumor using these compositions are also included, wherein an effective amount of the composition is administered to a patient in need of such treatment.

The antigen-binding fragment of the antibody can be a single chain Fv fragment, an F(ab') fragment, an F(ab) fragment, and an $F(ab')_2$ fragment, or any other antigen-binding fragment. In a specific embodiment, infra, the antibody or fragment thereof is a human IgG isotype antibody.

Naturally, the present invention extends to the immortalized human B memory lymphocyte and B cell, respectively, that produces the antibody having the distinct and unique characteristics as defined below.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region as set forth in FIG. 4 (SEQ ID NOs: 5 to 10).

Accordingly, the present invention also encompasses vectors comprising said polynucleotides and host cells transformed therewith as well as their use for the production of an antibody and equivalent binding molecules which are specific for antigens that are indicative and/or causative for a tumor, in particular for melanoma or breast cancer.

The antibody, immunoglobulin chain(s), binding fragments thereof and antigen binding to said antibody can be used in pharmaceutical and diagnostic compositions for tumor immunotherapy and diagnosis, respectively. The use of the foregoing compositions in the preparation of a medicament is however preferred.

Hence, it is a particular object of the present invention to provide methods for treating or preventing a cancerous disease such as primary breast carcinoma and metastases. The methods comprise administering an effective concentration of an antibody or antibody derivative to the subject where the antibody targets tumor tissue and cells.

Further embodiments of the present invention will be apparent from the description and Examples that follow. Furthermore, the description of the present invention, where necessary or appropriate, may be supplemented with the disclosure content of applicant's earlier European patent application EP 07 005 180.0 filed with the European Patent Office on Mar. 13, 2007.

BRIEF DESCRIPTION OF THE DRAWINGS

FIG. 4: Amino acid and nucleotide sequences of the variable region, i.e. heavy chain (amino acid sequence as set forth in SEQ ID NO: 2 and nucleotide sequence as set forth in SEQ ID NO: 1) and kappa light chain (amino acid sequence as set forth in SEQ ID NO: 4 and nucleotide sequence as set forth in SEQ ID NO: 3) of antibody 12D7. Complementarity determining regions (CDRs) are underlined. CDR1 of the variable heavy chain region is set forth in SEQ ID NO: 5, CDR2 in SEQ ID NO: 6 and CDR3 in SEQ ID NO: 7. CDR1 of the variable light chain region is set forth in SEQ ID NO: 8, CDR2 in SEQ ID NO: 9 and CDR3 in SEQ ID NO: 10.

DETAILED DESCRIPTION OF THE INVENTION

Figure 1:
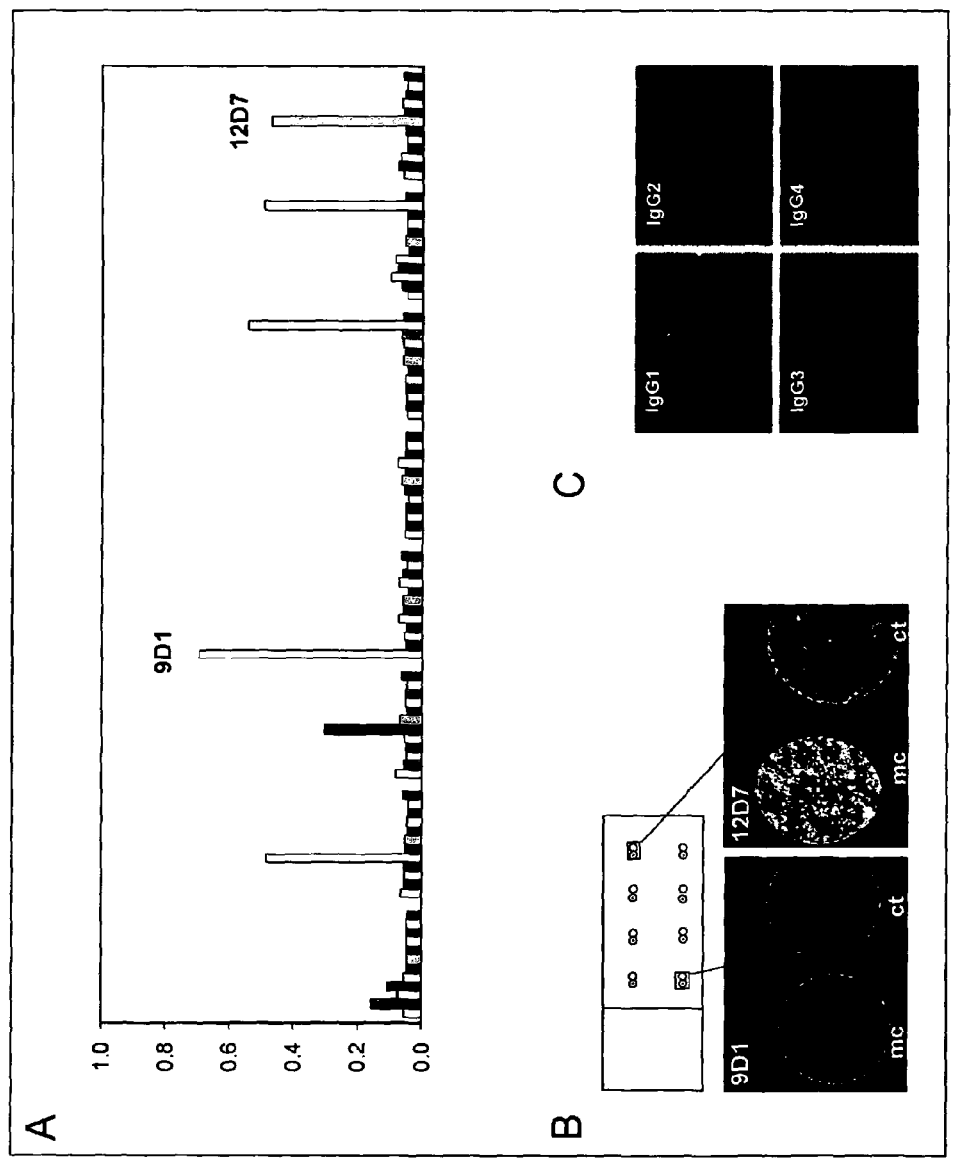
FIG. 1: Memory B cell culture well 12 D7 contains antibodies specific for NY-ESO-1. Medium conditioned by memory B cell cultures was assayed for the presence of NY-ESO-1-specific human antibodies A) In ELISA displaying full length recombinant NY-ESO-1. B) In immunohistochemistry on NY-ESO-1-positive mamma carcinoma (mc) and on NY-ESO-1-negative control tissue (ct). Shown is the staining obtained with conditioned medium of two ELISA-positive memory B cell culture wells (9D1, 12D7). C) NY-ESO-1-specific antibody contained in well 12D7 is of the IgG1 subclass as demonstrated by the staining of NY-ESO-1-positive tissue with B cell conditioned medium from culture well 12D7 followed by secondary antibodies against IgG subclasses IgG1-4.

The present invention generally relates to antibodies and antigen-binding fragments thereof, which demonstrate the immunological binding characteristics and/or biological properties as outlined for the antibody illustrated in the Examples. Where present, the term "immunological binding characteristics," or other binding characteristics of an antibody with an antigen, in all of its grammatical forms, refers to the specificity, affinity, cross-reactivity, and other binding characteristics of an antibody. Naturally, the present invention extends to the antibody producing cell lines and recombinant cells as well. The present invention further relates to diagnostic assays and kits that comprise the binding molecule of the present invention and to therapeutic methods based thereon.

In accordance with the present invention a human antibody specific for the tumor-associated antigen NY-ESO-1 was cloned from a melanoma patient who was seropositive for NY-ESO-1 in ELISA and on autologous tumor sections by using a method for identifying, validating and producing tumor diagnostically and therapeutically useful binding molecules essentially as disclosed in applicant's co-pending international application PCT/EP2008/000053 "Method of providing disease-specific binding molecules and targets", filed on Jan. 7, 2008, the disclosure content of which is incorporated herein by reference. The screening of antibody candidates was performed on ELISA and on tumor tissue using an adaptation of the tissue microarray technology. The obtained tissue-reactive human monoclonal antibody was shown to bind to the N-terminus of NY-ESO-1 that is also shared by the tumor-associated antigen LAGE-1; see Example 3.

Unless stated otherwise, the terms "cancer" and "tumor" are used interchangeably herein.

For the sake of clarity only and without restricting the scope of the present invention most of the following embodiments are discussed with respect to human antibodies and antibody-like molecules which represent the preferred binding molecules for the development of therapeutic and diagnostic agents in accordance with the present invention. However, it is to be understood that as used in context of the present invention the term "antibody", and fragment thereof, may also refer to other non-antibody binding molecules that bind to a human derived tumor (associated) antigen NY-ESO-1 including but not limited to hormones, receptors, ligands, major histocompatibility complex (MHC) molecules, chaperones such as heat shock proteins (HSPS) as well as cell-cell adhesion molecules such as members of the cadherin, integrin, C-type lectin and immunoglobulin (Ig) superfamilies.

NY-ESO-1 has been originally identified in an esophageal cancer patient using an antibody-based cloning technique (SEREX, see infra). Recently it could be shown that NY-ESO-1 may represent the most immunogenic CT antigen, because spontaneous cellular and humoral immune responses can be observed in a high percentage of patients with NY-ESO-1 expressing tumors (Gnjatic et al., Proc. Natl. Acad. Sci. USA 100 (2003), 8862-8867; Jager and Knuth, Breast 14 (2005), 631-635).

Since CT antigens are selectively expressed in human tumor cells and in spermatogonias of the testis, they represent a promising group of target antigens for an immunotherapeutic approach in cancer patients. Among them, NY-ESO-1 appears to be strongly immunogenic and is known to induce an efficient humoral and cellular immune response in patients with melanoma and ovarian, breast, lung, as well as bladder cancer making it an ideal target for active cancer immunotherapy. For information on the nucleotide and amino acid sequences as well as origin, primary literature, etc. of tumor antigens and tumor associated antigens see appropriate databases such as UniProtKB/Swiss-Prot hosted by EMBL, in which an entry for NY-ESO-1 may be found under primary accession number P78358.

In a particularly preferred embodiment, the antibody of the present invention binds to an epitope defined by an amino acid sequence set forth in SEQ ID NO: 11 representing the amino acid residues 11 to 30 of the NY-ESO-1 protein.

Means and methods for the recombinant production of antibodies and mimics thereof as well as methods of screening for competing binding molecules, which may or may not be antibodies, are known in the art; see also the Examples. However, as described herein, in particular with respect to therapeutic applications in human the antibody of the present invention is a human antibody in the sense that application of said antibody is substantially free of a human anti-murine antibody (HAMA) response otherwise observed for chimeric and even humanized antibodies.

Moreover, as demonstrated in appended Example 3, an antibody has been identified and cloned, which displays particularly high binding affinity with a equilibrium dissociation constant (KD) of the interaction with its cognate antigen in the lower nanomolar range. Preferably, the binding affinity of the binding molecule of the present invention with its cognate antigen is about at least $10^{-7}$M, more preferably at least $10^{-8}$M, particularly preferred $10^{-9}$M and still more preferred at least $10^{-10}$ M.

The present invention exemplifies human anti-NY-ESO-1 antibody and binding fragments thereof, which may be characterized by comprising in their variable region, i.e. binding domain at least one complementarity determining region (CDR) of the VH and/or VL of the variable region comprising the amino acid sequence depicted in FIG. 4 of (VH) (SEQ ID NO: 2) and (VL) (SEQ ID NO: 4). An exemplary set of CDRs of the above amino acid sequences of the $V_H$ and/or $V_L$ region as depicted in FIG. 4 are given in SEQ ID NOs: 5 to 10. However, as discussed in the following the person skilled in the art is well aware of the fact that in addition or alternatively CDRs may be used, which differ in their amino acid sequence from those set forth in SEQ ID NOs: 5 to 10 by one, two, three or even more amino acids in case of CDR2 and CDR3.

In one embodiment, the antibody of the present invention is any one of an antibody comprising an amino acid sequence of the $V_H$ and/or $V_L$ region as depicted FIG. 4. Alternatively, the antibody of the present invention is an antibody or antigen-binding fragment thereof, which competes for binding to the NY-ESO-1 antigen with at least one of the antibodies having the $V_H$ and/or $V_L$ region as depicted in FIG. 4. Those antibodies may be murine as well, however, humanized, xenogeneic, or chimeric human-murine antibodies being preferred, in particular for therapeutic applications. An antigen-binding fragment of the antibody can be, for example, a single chain Fv fragment (scFv), a F(ab') fragment, a F(ab) fragment, or an F(ab')$_2$ fragment.

Thus, for some applications only the variable regions of the antibodies are required, which can be obtained by treating the antibody with suitable reagents so as to generate Fab', Fab, or F(ab")$_2$ portions. Such fragments are sufficient for use, for example, in immunodiagnostic procedures involving coupling the immunospecific portions of immunoglobulins to detecting reagents such as radioisotopes.

As an alternative to obtaining immunoglobulins directly from the culture of immortalized B cells or B memory cells, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include CHO cells, HEK 293 cells, or NSO cells. The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In another embodiment the present invention relates to NY-ESO-1 antigen which is recognized by the antibody of the present invention described hereinbefore, both in peptide form and in post translational modified form, wherein the antigen is preferably a peptide consisting of least 6-50, and preferably no more than 10-100 amino acids in length, which contain the cognate epitope. Most preferably, the antigen of the present invention comprises the amino acid sequence of SEQ ID NO: 11 and consists of about 10 to 30 amino acids, and preferably is no more than about 20 amino acids in length. The molecule is large enough to be antigenic without any posttranslational modification, and hence it is useful as an immunogen, when combined with an adjuvant (or without it), in both precursor and post-translationally modified forms. These antigens and peptides can be used to determine whether or not antibodies are present in a sample, such as serum or blood. Preferably, the antigen of the present invention is capable of eliciting a humoral response in human.

In accordance with the above, the present invention also relates to a polynucleotide encoding the antigen or binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody. The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs" and refer to the amino acid residues of an antibody which are responsible for antigen-binding. The hypervariable regions or CDRs of the human IgG subtype of antibody comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed Public Health Service, National Institutes of Health, Bethesda, Md (1991) and/or those residues from a hypervariable loop, i.e. residues 26-32 (L1), 50-52 (L2) and 91-96 (L3) in the light chain variable domain and 26-32 (H1), 53-55 (H2) and 96-101 (H3) in the heavy chain variable domain as described by Chothia et al., J. MoI. Biol. 196 (1987), 901-917. Framework or FR residues are those variable domain residues other than and bracketing the hypervariable regions. The term "specific binding" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a nonspecific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen". As used herein "highly specific" binding means that the relative $K_D$ of the antibody for the specific target epitope, i.e. taa NY-ESO-1 is at least 10-fold less than the $K_D$ for binding that antibody to other ligands. Preferably, the antibody binds its cognate NY-ESO-1 antigen with a dissociation constant $(K_D)$ of $10^{-9}$ M or less.

The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, NY (1984), Kuby, Janis Immunology, W. H. Freeman and Company New York, NY (1992), and methods described herein. The measured affinity of a particular antibody-antigen interaction can vary if measured under different conditions, e.g., salt concentration, pH. Thus, measurements of affinity and other antigen-binding parameters, e.g., K sub D, IC50, are preferably made with standardized solutions of antibody and antigen, and a standardized buffer.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in European patent applications EP 0 451 216 A1 and EP 0 549 581 A1. Furthermore, the person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in SEQ ID NOs: 5 to 10.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions.

Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the $P_L$, lac, trp or tac promoter in E. coli, and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979).

Furthermore, the present invention relates to vectors, particularly plasmids, cosmids, viruses and bacteriophages used conventionally in genetic engineering that comprise a polynucleotide encoding the antigen or preferably a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well known methods, which vary depending on the type of cellular host. For example, calcium chloride transfection is commonly utilized for prokaryotic cells, whereas calcium phosphate treatment or electroporation may be used for other cellular hosts; see Sambrook, supra.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably HEK 293, NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

Thus, in a further embodiment, the present invention relates to a method for the production of an antigen of the present invention or of an antibody or a binding fragment or immu-noglobulin chain(s) thereof, said method comprising
(a) culturing a cell as described above; and
(b) isolating said antigen, antibody or binding fragment or immunoglobulin chain(s) thereof from the culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or its corresponding immunoglobulin chain(s) of the invention can then be isolated from the growth medium, cellular lysates, or cellular membrane fractions. The isolation and purification of the, e.g., recombinantly expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

As mentioned before, the immunoglobulin or its encoding cDNAs may be further modified. Thus, in a further embodiment the method of the present invention comprises any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. Further sources of antibodies to be utilized in accordance with the present invention are so-called xenogeneic antibodies. The general principle for the production of xenogeneic antibodies such as human antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses small peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide.

Hence, the present invention relates to any binding molecule, antibody or binding fragment which are obtainable in accordance with above described means and display the mentioned properties, i.e. which specifically recognize NY-ESO-1, and which for therapeutic use preferably maintain a substantially human framework so as to be devoid of immunogenicity in a patient.

In a further embodiment of the present invention, the antibody, immunoglobulin chain or a binding fragment thereof or the antigen is detectably labeled. Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, Int. J. Cancer Surp. SuDP 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, J. Infect Disease 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, Cancer Treat. Res. 68 (1993), 181-194 and by Fanger, Crit. Rev. Immunol. 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

The above described fusion protein may further comprise a cleavable linker or cleavage site for proteinases. These spacer moieties, in turn, can be either insoluble or soluble (Diener et al., Science 231 (1986), 148) and can be selected to enable drug release from the antigen at the target site. Examples of therapeutic agents which can be coupled to the antibodies and antigens of the present invention for immunotherapy are drugs, radioisotopes, lectins, and toxins. The drugs with which can be conjugated to the antibodies and antigens of the present invention include compounds which are classically referred to as drugs such as mitomycin C, daunorubicin, and vinblastine. In using radioisotopically conjugated antibodies or antigens of the invention for, e.g., tumor immunotherapy, certain isotopes may be more preferable than others depending on such factors as leukocyte distribution as well as stability and emission. Depending on the autoimmune response, some emitters may be preferable to others. In general, α and β particle emitting radioisotopes are preferred in immunotherapy. Preferred are short range, high energy α emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pdd and $^{188}$Re. Other therapeutic agents which can be coupled to the antibody or antigen of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or the corresponding vectors instead of the proteinaeous material itself.

Hence, the biological activity of the antibody and binding domain identified here suggests that they have sufficient affinity to make them potential candidates for drug localization to cells expressing the appropriate surface structures of the diseased cell and tissue, respectively. This targeting and binding to cells could be useful for the delivery of therapeutically or diagnostically active agents and gene therapy/gene delivery. Molecules/particles with an antibody of the invention would bind specifically to cells/tissues expressing the NY-ESO-1 antigen, and therefore could have diagnostic and therapeutic use. Thus, the antibody or the antigen of the present invention can be labeled (e.g., fluorescent, radioactive, enzyme, nuclear magnetic, heavy metal) and used to detect specific targets in vivo or in vitro including "immunochemistry" like assays in vitro. In vivo they could be used in a manner similar to nuclear medicine imaging techniques to detect tissues, cells, or other material expressing the NY-ESO-1 antigen. Thus, in a further embodiment the present invention relates to the use of an antibody of the present invention or binding fragment thereof for the preparation of a composition for in vivo detection of or targeting a therapeutic and/or diagnostic agent to a tumor.

Moreover, the present invention relates to compositions comprising the aforementioned antibody or binding fragment or antigen of the present invention or chemical derivatives thereof, or the polynucleotide, vector or cell of the invention. The composition of the present invention may further comprise a pharmaceutically acceptable carrier. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Furthermore, the pharmaceutical composition of the present invention may comprise further anti-tumor agents such as interleukins or interferons depending on the intended use of the pharmaceutical composition. Hence, in a particular preferred embodiment the present invention relates to the use of the antibody or binding fragment of the present invention or of a binding molecule having substantially the same binding specificities of any one thereof, the antigen, the polynucleotide, the vector or the cell of the present invention for the preparation of a pharmaceutical or diagnostic composition for the preparation of a pharmaceutical or diagnostic composition for treating or preventing the progression of a tumor; for the amelioration of symptoms associated with a tumor; for diagnosing or screening a subject for the presence of a tumor or for determining a subject's risk for developing a tumor. Said pharmaceutical composition can be designed to be administered intravenously, intramuscularly, subcutaneously, intraperitoneally, intranasally, parenterally or as an aerosol; see also infra.

Hence, in one embodiment the present invention relates to a method of treating or preventing the progression of a tumor in a subject; for ameliorating the symptoms associated with a tumor; for diagnosing or screening a subject for the presence of a tumor or for determining a subject's risk for developing a tumor, which method comprises administering to said subject an effective amount of any one of the afore-described antibodies, antigens, polynucleotides, vectors or cells of the instant invention. In particular, the therapeutic and diagnostic applications in accordance with the present invention include melanoma and breast cancer, and are most suitable for use in targeting a tumor comprising primary breast carcinoma and/or metastases. Unless stated otherwise, the terms "tumor", "cancer", "carcinoma" and the like are used interchangeably herein.

Hence, the present invention encompasses any use of a tumor antigen binding molecule comprising at least one CDR of the above described human antibody, in particular for diagnosing and/or treating a disorder related to a tumor. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen binding site.

In another embodiment the present invention relates to a diagnostic composition comprising any one of the above described antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the binding antibodies of the present invention may also be used in a method for the diagnosis of a tumor in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the tumor in the tested individual. In the same manner, the specific antigen bound by the antibodies of the invention may also be used. Thus, the present invention relates to an in vitro immunoassay comprising the antibody or the antigen of the invention. A preferred embodiment of the present invention relates to the determination of cancer, melanoma and breast cancer in particular. The methods involve assaying for NY-ESO-1.

In one embodiment, the present invention relates to a method for determining status of a cancerous condition, e.g., regression, progression of onset of a cancerous condition in a patient with a tumor that expresses tumor (associated) antigen NY-ESO-1, comprising assaying a sample taken from said patient for antibodies which specifically bind to said antigen, and comparing a value obtained to a prior value obtained following assay of a prior sample taken from said patient, any difference there between being indicative of a change in status of said cancerous condition. A corresponding method that can be employed in accordance with the present invention is disclosed in international application WO01/07917. Alternatively, such method may be performed with an antibody of the present invention.

In another embodiment, the present invention relates to a method for determining cancer cells, e.g., breast cancer cells in a sample comprising assaying said sample for expression of NY-ESO-1 by assaying for presence of NY-ESO-1 protein with an antibody of the present invention, wherein expression of NY-ESO-1 is indicative of the presence of cancer cells in said sample. A similar method which may be adapted in accordance with the present invention is described in U.S. Pat. No. 6,338,947 for SCP-1, NY-ESO-1 and SSX-2.

In this context, the present invention also relates to means specifically designed for this purpose. For example, a protein- or antibody-based array may be used, which is for example loaded with either the antigen of the present invention in order to detect autoantibodies which may be present in patients suffering from a tumor, in particular metastases, or with antibodies or equivalent antigen-binding molecules of the present invention. Design of microarray immunoassays is summarized in Kusnezow et al., Mol. Cell. Proteomics 5 (2006), 1681-1696. Accordingly, the present invention also relates to microarrays loaded with antibody or antigen of the present invention.

The present invention also provides a pharmaceutical and diagnostic, respectively, pack or kit comprising one or more containers filled with one or more of the above described ingredients, i.e. antibody or binding fragment thereof, antigen, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, i.e. kit of the present invention is of course particularly suitable for the diagnosis, prevention and treatment of a disorder which is accompanied with the presence of tumor-associated antigen NY-ESO, in particular applicable for the treatment of tumors as mentioned above.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease. Furthermore, the term "subject" or "patient" refers to a mammal, preferably a human, in need of treatment for a condition, disorder or disease.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intra-muscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as anti-tumor agents and cytotoxic drugs, depending on the intended use of the pharmaceutical composition. Furthermore, the pharmaceutical composition may also be formulated as a vaccine, for example, if the pharmaceutical composition of the invention comprises an antibody of the present invention for passive immunization or cognate antigen for active immunization. Vaccine formulations for the treatment of cancer employing tumor associated antigens such as NY-ESO-1 are described for example in international application WO2005/105139. In addition, co-administration or sequential administration of other agents may be desirable.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Preferably, the therapeutic agent in the composition is present in an amount sufficient to prevent metastasis and neoplastic growth of cells.

The pharmaceutical compositions in accordance with the present invention can preferably be used for the treatment of tumors and cancer including but not limited to melanoma, primary breast cancer, hepatocellular carcinoma and metastases.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using interne search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Supplementary Methods

Patient Material

Tumor material as well as normal tissue not necessary for the routine histopathological analysis was frozen in liquid nitrogen. Serum and blood for the isolation of memory B cells was collected from patient C1 in accordance with the informed consent that was approved by the local Ethical committee and signed by the patient.

Memory B Cell Culture

Memory B cells were isolated from human peripheral blood lymphocytes by a two step selection procedure. The pan B cell marker CD22 was used for the positive selection of B cells using the MACS technology (Miltenyi, Bergisch Gladbach, Germany). PBL were labeled using MACS-conjugated anti human CD22 mAbs, phycoerythrin-conjugated mAbs anti human IgD and APC-conjugated antibodies anti human IgM, IgA, CD3, CD8, CD56 (Becton Dickinson, Basel, Switzerland). Pan B cells were isolated by positive selecting CD22-positive cell using a midi MACS device and LS columns (Miltenyi) followed by selection of phycoerythrin- and APC-negative cells using a MoFlo cell sorter (Dako-Cytomation, Fort Collins, USA). CD22-positive IgM-, IgD-, IgA-negative B cells were then incubated with EBV containing supernatant obtained from B95-8 cells in the presence of CpG 2006 (6, 15) in B cell medium containing RPMI 1640 supplemented with 10% fetal calf serum. Cells were seeded in at 50 cells per well in B cell medium on 30.000 irradiated feeder PBL prepared from voluntary donors.

After 2 weeks of culture the conditioned medium of memory B cell cultures was screened for the presence of NY-ESO-1-specific antibodies by ELISA and on NY-ESO-1-positive autologous and non-autologous tissue sections.

ELISA 96 well strip well microplates (Corning, N.Y., USA) were coated with 25 µl/well of a 1 µg/ml recombinant NY-ESO-1 protein in PBS overnight at 4° C. Plates were washed with PBS-T and blocked overnight at 4° C. with PBS containing 5% milk powder (Rapilait, Migros, Switzerland). B cell conditioned medium, patient serum and recombinant antibody preparations were incubated for 2 h at room temperature. Binding of human antibodies to NY-ESO-1 was determined using a donkey anti-human IgG-HRP secondary antibody (Jackson ImmunoResearch Europe Ltd., Cambridgeshire, UK) followed by measurement of the HRP activity using a TMB substrate solution (TMB, Sigma, Buchs, Switzerland).

Epitope Mapping ELISA 20 mer peptides spanning the entire NY-ESO-1 protein with 10 aa overlaps shared by each adjacent peptides (Peptides&Elephants, Nuthetal, Germany) were used to coat Maxisorp ELISA plates (Nunc, Rochester, N.Y.). Human recombinant antibody Manhattan or patient serum (diluted 1:500 in PBS) was detected using horseradish peroxidase-conjugated Goat anti-human IgG+IgM (Jackson ImmunoResearch).

Competition ELISA

Saturation experiments identified the half-maximal binding concentration of human monoclonal antibody Manhattan to NY-ESO-111-30 peptide as $1 \times 10^{-9}$ M or 0.15 µg/ml. In competition experiments, increasing concentrations of NY-ESO-111-30 peptide were mixed with Manhattan at a concentration of 0.15 µg/ml and the mix was then transferred to ELISA plates coated with NY-ESO-111-30.

Immunohistochemistry

Cylinders of tumor tissues measuring 0.6 mm in diameter were punched out of paraffin embedded NY-ESO-1-positive tumor tissue and healthy control tissue. Pairs formed of a cylinder of tumor tissue and of healthy control tissue were placed at each position of a 2×4 grid whose dimensions were compatible with the microtiter format of the B cell culture plates and conventional multi channel pipettes.

Immunohistochemistry was performed on formalin-fixed, paraffin-embedded tissue.

Heat-based antigen retrieval was applied to all slides. Non-specific fluorescence was blocked using polyclonal rabbit anti-human IgG (Dako, Baar, Switzerland) for 30 min at room temperature followed by a second block in 1% of low fat milk (Rapilait, Migros, Switzerland) for 10 min. Primary antibody or B cell conditioned medium was incubated overnight at 4° C. Binding of human antibodies to NY-ESO-1 was revealed using Cy 3-conjugated secondary antibodies to human IgG (Jackson ImmunoResearch Europe Ltd., Soham, UK). Staining of biotinylated recombinant human antibody Manhattan was revealed using Cy3- or HRP-conjugated streptavidin (Sigma, Buchs, Switzerland). As positive control for the presence of NY-ESO-1 antigen a mouse anti-NY-ESO-1 monoclonal antibody (Zymed, South San Francisco, USA) was used.

Analysis of immunofluorescence was performed on an inverted fluorescence microscope (Leica, Heerbrugg, Switzerland).

Single Cell-RT-PCR

Single cells obtained from a memory B cell culture were deposited into PCR tubes. cDNA was prepared using primers specific for the constant regions of immunoglobulin G heavy, light and γ-light chains. PCR amplification of immunoglobulin heavy and light chain variable regions was performed according to standard protocols (7, 16). Immunoglobulin heavy and light chain variable regions were amplified using a semi nested PCR approach. 1st round PCR was performed with primers specific for the IgG constant region and pools of primers specific for conserved framework 1 regions of heavy and light chain Ig variable region families (7). Subsequently, semi-nested PCR with nested primers specific for the IgG constant region and primers specific for framework 1 of heavy and light chain Ig variable region families that contained restriction sites were used as described (8). The immunoglobulin heavy and light chain PCR products were cloned into vectors containing the constant region of IgG1, IgKappa or IgLambda.

Antibody Production and Purification

293-T human embryonic kidney cells were cultured in DMEM supplemented with 10% ultra-low IgG FCS, 1% penicillin-streptomycin and 1% L-glutamin (Invitrogen, Basel, Switzerland). Co-transfection with immunoglobulin heavy and light chain encoding plasmid DNA was performed by the standard calcium phosphate precipitation method. Thereafter the cells were cultured in serum free D-MEM supplemented with 1% Nutridoma SP (Roche, Rotkreuz, Switzerland). Supernatants were collected after 8 days of culture and IgG was purified on a protein G column (Amersham Biosciences, Upsala, Sweden) using fast protein liquid chromatography (FPLC) (Amersham Biosciences, Upsala, Sweden). Purified Manhattan antibody was biotinylated following the manufacturers instructions (SIGMA, Buchs, Switzerland).

Immunofluorescence SK-MEL-37 Tumor Cells

SK-MEL-37 cells were grown onto microscope slide, fixed with formaldehyde and permeabilized with 1% Triton X-100 for 10 min at room temperature. After blocking with 10% goat serum for 1 h RT cells were incubated with Manhattan at a concentration of 1 ug/ml or negative control antibody (hu8-18c5 (17) expressed in recombinant fashion with a human Fc region) in PBS/1% goat serum/0.2% Triton X-100 overnight at 4°. Bound antibodies were visualized by staining with goat anti-human IgG Alexa Fluor® 546 (1:300, Molecular Probes, Leiden, Netherland) for 1 h RT. Microscopy was performed using a Leica SP 5 microscope.

EXAMPLE 1

Identification of NY-ESO-1-Specific B Cells from PBL of a Melanoma Patient

A melanoma patient was selected with a serum titer to the taa NY-ESO-1 in ELISA and on autologous lymph node sections obtained at biopsy. Post vaccination with recombinant vaccinia virus expressing full length NY-ESO-1 a partial clinical response demonstrated by the regression of two NY-ESO-1-positive metastases in the liver was observed. 50 ml Peripheral blood was collected from the patient and surface IgM/IgD double-negative B cells representing the Ig-switched memory B cells were isolated and cultured after immortalization using a modified Epstein Barr virus transformation protocol (6). 100.000 memory B cells were obtained and were seeded into 96 well microtiter templates at 50 cells per well. After 3 weeks of culture growing clones were observed in the culture wells and the medium conditioned by the B cell cultures was assayed for the presence of antibodies specific to NY-ESO-1. As a first screening an ELISA using recombinant full length NY-ESO-1 as antigen was performed. ELISA signals were rated as positive if they exceeded the background signal by a factor of three. This identified 9 ELISA-positive memory B cell culture wells out of the 2000 wells total. An example of the signal to noise ratio obtained with the ELISA is depicted in FIG. 1A. The ELISA-positive cultures were subsequently assayed in immunohistochemistry using NY-ESO-1-positive tumor tissue. The setup of the tissue screen consisted of 8 pairs of tissue rods of NY-ESO-1-positive mamma tumors and healthy mamma tissue as controls mounted on to glass slides. Due to the miniaturization of this assay 15 µl of B cell conditioned medium were sufficient to perform the assay. The ability to compare the conditioned medium of several memory B cell cultures and of negative controls on a single slide facilitated the evaluation of the fluorescence staining.

The evaluation of the 9 ELISA-positive B cell cultures in this tissue assay identified one culture that yielded a higher staining intensity as compared to that of the other 8. This is illustrated in FIG. 1B, where immunofluorescence obtained with tissue-reactive culture 12D7 is compared to immunofluorescence obtained with well 9D1 which was rated as being not tissue-reactive.

Since IgG-subclass information on the NY-ESO-1-specific antibody would have been lost in the molecular cloning step it was determined at this step using immunohistochemistry with NY-ESO-1-positive tissue sections in combination with subclass-specific secondary antibodies anti human IgG1, IgG2, IgG3 and IgG4. As shown in FIG. 1C, tissue staining for NY-ESO-1 is only observed with a secondary antibody anti IgG1.

EXAMPLE 2

Molecular Cloning of an NY-ESO-1-Specific Antibody Secreted by Cultured Memory B Cells Previous attempts at the cellular cloning of identified antigen-specific EBV-transformed human memory B cells had not been successful. Therefore, in accordance with the present invention it was embarked on a molecular cloning strategy based on RT-PCR of single sorted cells harvested from well 12D7 in order to isolate the antibody clone responsible for the above described staining pattern. 32 cells were harvested and deposited as single cells directly into PCR tubes.

After cDNA synthesis, the heavy and light chain variable regions of human immunoglobulin were amplified using a nested PCR approach (7). Heavy and kappa light chain sequences with 16 of the 32 sorted cells were obtained. PCR for lambda light chain variable sequences did not give a product with any of the cells. Sequence analysis identified 4 distinct antibody clones which were numbered according to their relative abundance. Clone 1 was found in eight of the 16 cells, clone 2 in four cells and clones 3 and 4 each in two cells. It was then determined whether one of these four clones when expressed as recombinant antibody yielded a similar NY-ESO-1 staining as observed with conditioned medium from B cell culture well 12D7. To that end, the heavy and light chain variable sequences were cloned into antibody expression vectors that provided the constant regions of the human IgG1 heavy chain and of the human kappa light chain (8). The constant regions of IgG1 were used since the NY-ESO-1-specific antibody identified in conditioned medium of well 12D7 was determined to be of this subclass (FIG. 1 C).

Figure 2:
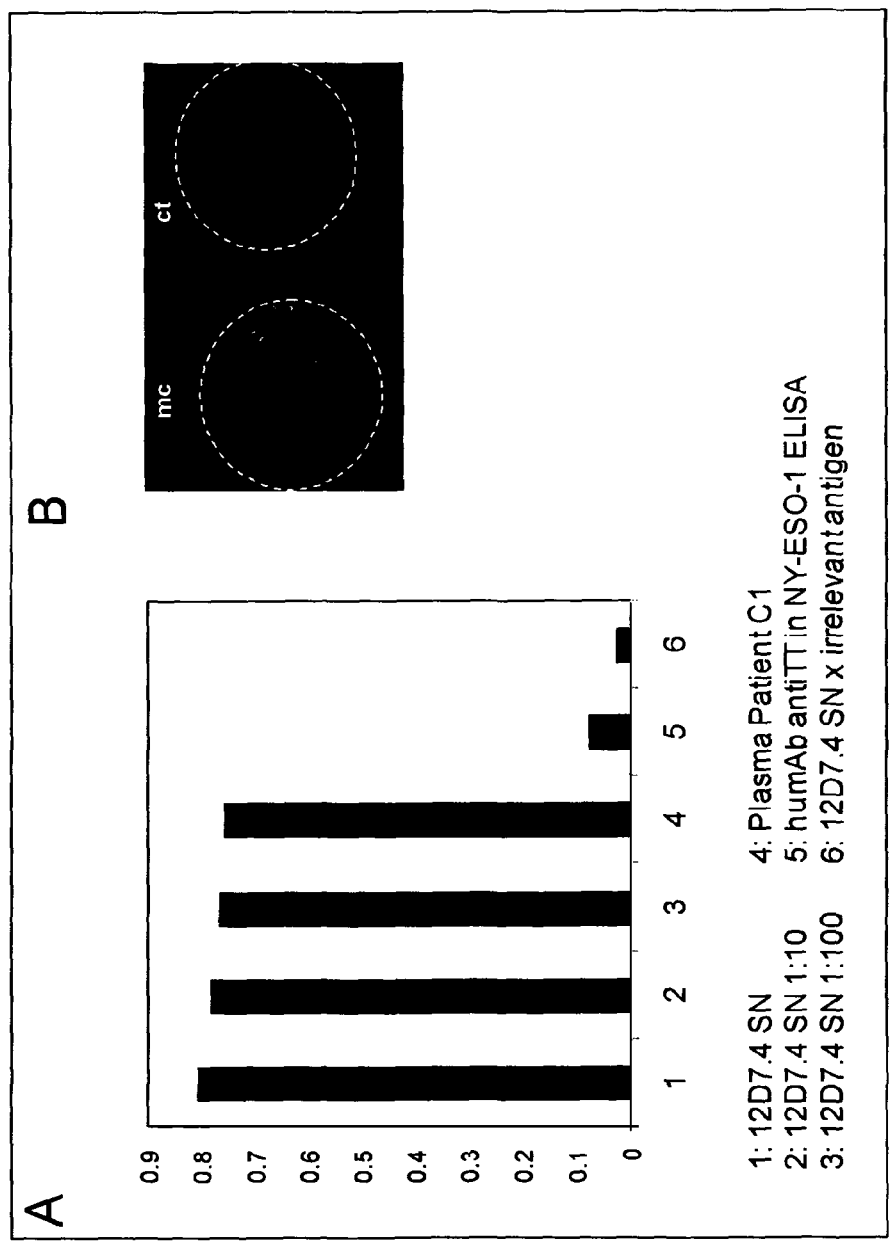
FIG. 2: Recombinant human antibody 12D7 clone number 4 obtained by single cell RT-PCR of cultured memory B cells specifically recognizes NY-ESO-1 in ELISA and on tissue sections. Supernatant fluid (SN) harvested from 293T HEK cells transfected with immunoglobulin heavy and light chain expression vectors expressing clone 12D7 number four was tested for specificity to NY-ESO-1 in A) ELISA displaying full length NY-ESO-1. ELISA values are indicated for undiluted SN (1:12 D7.4 SN) a 1/10 dilution (2:12 D7.4 SN) and a 1/100 dilution (3:12 D7.4 SN). For comparison, the ELISA signal obtained with plasma of the patient from which the memory B cell cultures were derived used as a 1/100 dilution is also shown (4). As controls, the absence of binding to NY-ESO-1 coated ELISA plates of SN obtained upon transfection of an irrelevant recombinant antibody produced in the same way as 12D7.4 is shown (5) as well as the absence of binding of 12D7 clone No. 4 to ELISA plates coated with an irrelevant antigen. B) Immunohistochemistry on NY-ESO-1-positive mamma carcinoma (mc) and on NY-ESO-1-negative control tissue (ct) shows specific binding of recombinant 12D7 clone No. 4 to mamma carcinoma.

Functional analysis of the four clones was performed by re-screening the recombinant antibodies in ELISA and on NY-ESO-1-positive tissue sections. To that end, heavy chain and corresponding light chain expression vectors of the four clones were transfected into 293 HEK cells and the supernatant fluid of the transfected cells was tested directly in ELISA and immunohistochemistry. All four supernatant fluids produced functional IgG1 as tested in anti-human-IgG-ELISA. While clones 1-3 did not show any binding to NY-ESO-1 in ELISA clone number 4 was positive up to the last dilution tested (1/100) (FIG. 2 A). This clone also showed a specific staining in immunohistochemistry using NY-ESO-1-positive tissue sections (FIG. 2 B).

This was taken as confirmation that the sequence of the immunoglobulin variable regions of the original NY-ESO-1-specific antibody as it occurred in the patient had been retrieved. For the sake of simplicity clone 12D7No. 4 was named "Manhattan" and used for further characterization using protein G purified material obtained from transiently transfected HEK cells.

EXAMPLE 3

Figure 3:
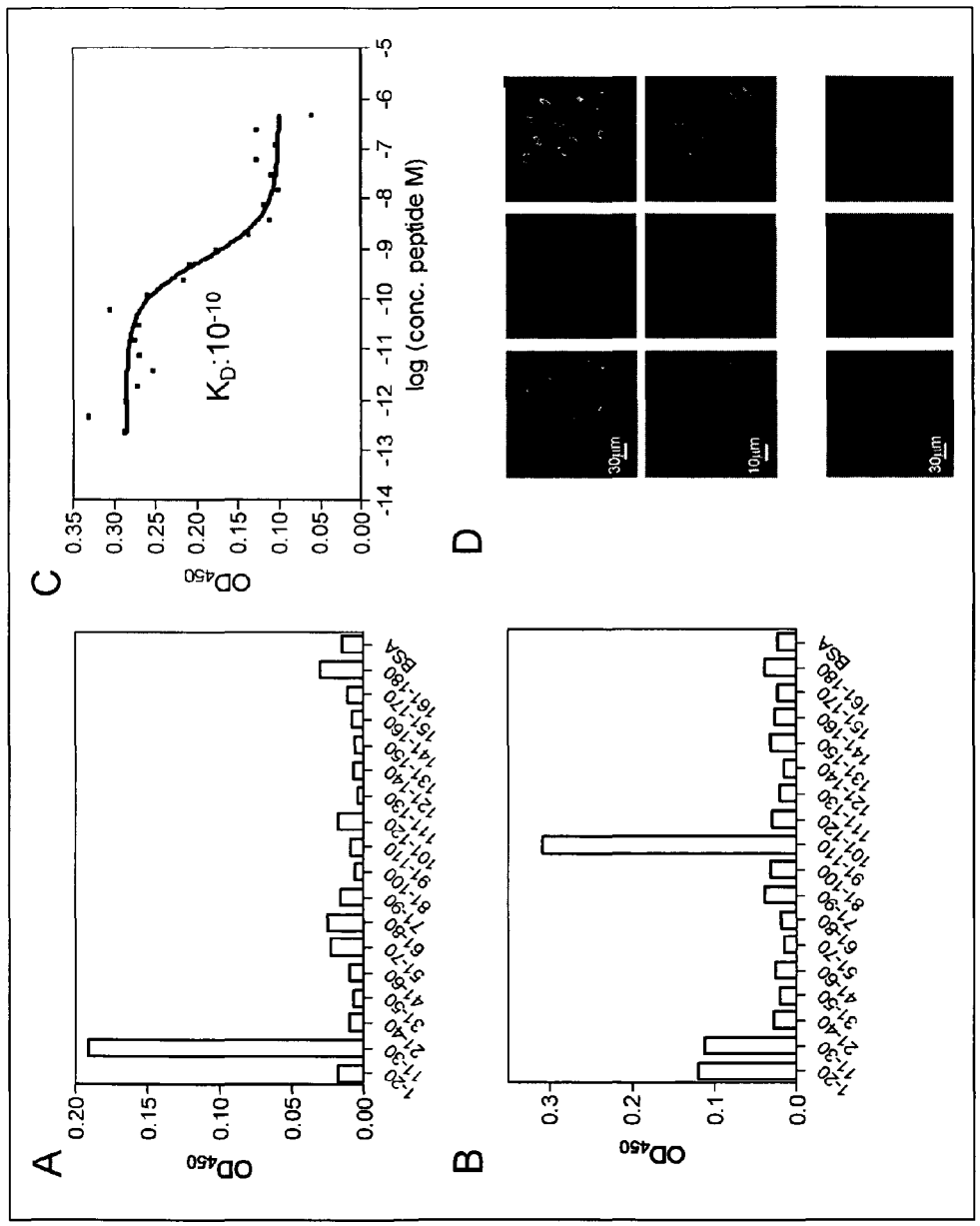
FIG. 3: Characteristics of human monoclonal antibody Manhattan. Epitope mapping was performed using overlapping peptides spanning the entire NY-ESO-1 protein coated onto ELISA plates. A) Manhattan specifically binds to a peptide spanning amino acids 11 to 30 at the N-terminus of the NY-ESO-1 protein. B) serum of patient C1 recognizes various peptide fragments at the N-terminus and the mid-region of NY-ESO-1. C) Competition ELISA experiments with NY-ESO-$1_{11-30}$ peptide determine the avidity of Manhattan as KD=$10^{-10}$. D) Immunofluorescence staining of NY-ESO-1-positive cell line SK-MEL-37 with humAb Manhattan shows co-localization of NY-ESO-1 staining with nuclear marker Hoechst. Control antibody human recombinant 8-15c5 specific for MOG does not bind.

NY-ESO-1 Specific Human Monoclonal Antibody Manhattan Binds to Peptide NY-ESO-1$_{11-30}$ with a KD of $10^{-10}$ To identify the epitope recognized by Manhattan on NY-ESO-1 ELISA was performed using overlapping peptides spanning the complete NY-ESO-1 protein. As shown in FIG. 3A, Manhattan binds to a peptide representing the amino acids 11 to 30 from the NY-ESO-1 protein but not to the two adjacent peptides that span amino acids 1-20 or 21-40. This suggests that the epitope recognized by Manhattan lies at the junction of these two peptides around amino acid 20 of NY-ESO-1. This epitope, among others was also recognized by antibodies contained in serum of patient C1 (FIG. 3B).

The avidity of Manhattan was determined by competition ELISA using increasing concentrations of soluble NY-ESO-1$_{11-30}$ peptide to compete for the plate bound peptide. As depicted in FIG. 3C, the antigen-binding equilibrium dissociation constant (KD) of the interaction of Manhattan with its cognate peptide was in the lower nanomolar range.

As a final assay used in the characterization of human monoclonal antibody Manhattan immunofluorescence analysis on the NY-ESO-1-positive cell line SK-MEL-37 was performed (9). Staining of this cell line with Manhattan resulted in a nuclear signal that co-localized with staining obtained with the nuclear marker Hoechst.

Conclusion

The above experiments provide a general method for the identification and molecular cloning of antibodies directly from peripheral blood lymphocytes (PBLs) of human subjects. The method of the present invention could be proven by isolating a human monoclonal antibody to the tumor-associated antigen NY-ESO-1 from a melanoma patient. Starting with the screening of antibodies secreted by cultures of short term immortalized human memory B cells cultures that were positive in ELISA and in immunohistochemistry on NY-ESO-1 positive tissue were identified. This primary screen was followed by a molecular cloning step the purpose of which was to identify and isolate the single clone of B cells that secreted the antibody detected in the primary screening. The presence of only 4 different clones in well 12D7 as revealed by sequence analysis after single-cell RT-PCR, suggests, that of the initially 50 cells that were seeded only few had been immortalized and survived.

A subsequent secondary screen of the recombinant candidate antibodies resulted in the identification of a single monoclonal antibody with an identical staining pattern as the original antibody that was produced by the cultured memory B cells derived from patient PBL. Thus, an antibody as it occurred originally in the patient could successfully be retrieved. This antibody, coined "Manhattan" recognizes a N-terminal epitope around amino acid position 20 which is shared between NY-ESO-1 and the taa LAGE-1 (9). This epitope is also recognized by serum of patient C1 supporting the notion of Manhattan as being a genuine copy of an antibody that occurred in the patient.

As of to date Manhattan is the first human monoclonal antibody to NY-ESO-1 it may also be the first patient-derived affinity matured antibody to a tumor antigen and taa, respectively. This novel method of the present invention bypasses some of the difficulties inherent to EBV-transformation of B cells such as genetic instability and poor cloning efficiency (6, 10). While the isolation of human monoclonal antibodies from EBV-immortalized memory B cells had been successfully performed in a previous study (6), it is noteworthy to mention that previous attempts tried prior to the above described method of the present invention at the isolation of NY-ESO-1 specific antibodies from the same patient using EBV-transformation and cellular cloning techniques failed despite a considerable number of memory B cell cultures identified in the cellular screening.

A second object of the present invention was the isolation of an antibody to the tumor-associated antigen NY-ESO-1 with tissue-reactivity. This was motivated by the observation, that serum of the patient contained antibodies that reacted with NY-ESO-1-positive autologous tissue taken at biopsy. To that end the micro-array technology was adapted for the screening of memory B cell cultures. This had several advantages as compared to classical methods of immunohistochemistry. First, the availability on one single slide of several replica positions allowing to assay and to compare several samples. Second, the possibility to place positive tissue adjacent to negative tissue greatly improves assay sensitivity, a feature which was crucial since incubation with conditioned medium of memory B cell cultures often resulted in very weak staining. Third, this miniaturization of the assay format needs much less of conditioned medium which also is a decisive factor since the culture volume of memory B cell cultures was generally less than 200 µl.

The observation that serum of the patient and human monoclonal antibody Manhattan recognized fixed tissue sections may be irrelevant for the situation in vivo at least with regard to a direct therapeutic role via the induction of antibody induced immune effector mechanisms acting on a cellular level to clear NY-ESO-1-positive cells. NY-ESO-1 has been described as an intracellular antigen (11) and was shown in this study to be localized in the nucleus, at least in the cell line SK-Me-37. In this context, surface staining on live SK-Me-37 using biotinylated Manhattan had been negative.

The isolation of Manhattan constitutes a major step towards the evaluation of the therapeutic significance of patient-derived tumor-specific antibodies. There are several scenarios conceivable according to which such an antibody could mediate therapeutic effects. First, it could serve as an adjuvant for future vaccine protocols. Immune complexes formed upon co-administration of Manhattan with NY-ESO-1 could result in an increased induction of cellular immune responses (12).

A second possibility addresses the pathophysiological role of this class of antibodies in tumor patients. NY-ESO-1 frequently induces humoral responses which correlate with a bad prognosis for the patient (13). While this could be a mere correlation due to increased abundance of antigen as the tumor grows, a tolerogenic role of this B cell response could also be hypothesized. According to this scenario, free antigen released by necrotic or apoptotic tumor cells would induce a strong B cell response, the B cells then would present antigen as a result of Fc-receptor-mediated uptake of immune complexes (14). As B cells may be poor APC, this presentation could result in the induction of tolerance of NY-ESO-1-reactive T cells and thus prevent tumor rejection. The administration, in an early phase of tumor progression, of recombinant Manhattan F(ab)s could disrupt the uptake of antigen by B cells because F(ab) are not bound by Fc-receptors but would still capture antigen. This in turn, could prevent the tolerance induction in NY-ESO-1-specific T cells.

References

1. Sahin, U., Tureci, O., Schmitt, H., Cochlovius, B., Johannes, T., Schmits, R., Stenner, F., Luo, G., Schobert, I., and Pfreundschuh, M. Human neoplasms elicit multiple specific immune responses in the autologous host. Proc Natl Acad Sci USA, 92: 11810-11813, 1995.
2. Jager, E., Chen, Y. T., Drijfhout, J. W., Karbach, J., Ringhoffer, M., Jager, D., Arand, M., Wada, H., Noguchi, Y., Stockert, E., Old, L. J., and Knuth, A. Simultaneous humoral and cellular immune response against cancer-testis antigen NY-ESO-1: definition of human histocompatibility leukocyte antigen (HLA)-A2-binding peptide epitopes. J Exp Med, 187: 265-270, 1998.
3. Stevenson, F. K. Update on cancer vaccines. Curr Opin Oncol, 17: 573-577, 2005.
4. Davis, I. D., Chen, W., Jackson, H., Parente, P., Shackleton, M., Hopkins, W., Chen, Q., Dimopoulos, N., Luke, T., Murphy, R., Scott, A. M., Maraskovsky, E., McArthur, G., MacGregor, D., Sturrock, S., Tai, T. Y., Green, S., Cuthbertson, A., Maher, D., Miloradovic, L., Mitchell, S. V., Ritter, G., Jungbluth, A. A., Chen, Y.-T., Gnjatic, S., Hoffman, E. W., Old, L. J., and Cebon, J. S. Recombinant NY-ESO-1 protein with ISCOMATRIX adjuvant induces broad integrated antibody and CD4+ and CD8+ T cell responses in humans. PNAS 10.1073/, 101: 10697-10702, 2004.
5. Harris, M. Monoclonal antibodies as therapeutic agents for cancer. The Lancet Oncology, 5: 292, 2004.
6. Traggiai, E., Becker, S., Subbarao, K., Kolesnikova, L., Uematsu, Y., Gismondo, M. R., Murphy, B. R., Rappuoli, R., and Lanzavecchia, A. An efficient method to make human monoclonal antibodies from memory B cells: potent neutralization of SARS coronavirus. Nat Med, 10: 871-875, 2004.
7. Owens, G. P., Ritchie, A. M., Burgoon, M. P., Williamson, R. A., Corboy, J. R., and Gilden, D. H. Single-Cell Repertoire Analysis Demonstrates that Clonal Expansion Is a Prominent Feature of the B Cell Response in Multiple Sclerosis Cerebrospinal Fluid. J Immunol, 171: 2725-2733, 2003.
8. Wardemann, H., Yurasov, S., Schaefer, A., Young, J. W., Meffre, E., and Nussenzweig, M. C. Predominant autoantibody production by early human B cell precursors. Science, 301: 1374-1377, 2003.
9. Chen, Y. T., Gure, A. O., Tsang, S., Stockert, E., Jager, E., Knuth, A., and Old, L. J. Identification of multiple cancer/testis antigens by allogeneic antibody screening of a melanoma cell line library. Proc Natl Acad Sci USA, 95: 6919-6923, 1998.

10. Kuppers, R. B cells under influence: transformation of B cells by Epstein-Barr virus. Nat Rev Immunol., 3: 801-812, 2003.
11. Schultz-Thater, E., Noppen, C., Gudat, F., Durmuller, U., Zajac, P., Kocher, T., Heberer, M., and Spagnoli, G. C. NY-ESO-1 tumour associated antigen is a cytoplasmic protein detectable by specific monoclonal antibodies in cell lines and clinical specimens. Br J Cancer, 83: 204-208, 2000.
12. Woelbing, F., Kostka, S. L., Moelle, K., Belkaid, Y., Sunderkoetter, C., Verbeek, S., Waisman, A., Nigg, A. P., Knop, J., Udey, M. C., and von Stebut, E. Uptake of *Leishmania major* by dendritic cells is mediated by Fc{gamma} receptors and facilitates acquisition of protective immunity. J. Exp. Med., 203: 177-188, 2006.
13. Jager, E., Stockert, E., Zidianakis, Z., Chen, Y. T., Karbach, J., Jager, D., Arand, M., Ritter, G., Old, L. J., and Knuth, A. Humoral immune responses of cancer patients against "Cancer-Testis" antigen NY-ESO-1: correlation with clinical events. Int J Cancer, 84: 506-510, 1999.
14. Preiss, S., Kammertoens, T., Lampert, C., Willimsky, G., and Blankenstein, T. Tumor-induced antibodies resemble the response to tissue damage. Int J Cancer, 115: 456-462, 2005.
15. Hartmann, G. and Krieg, A. M. Mechanism and function of a newly identified CpG DNA motif in human primary B cells. J Immunol, 164: 944-953, 2000.
16. Barbas III, C. F. Phage Display A Laboratory Manual., Dennis R. Burtoon, Jamie K. Scott & Gregg J. Silverman (eds.) 2001). Dennis R. Burtoon, Jamie K. Scott & Gregg J. Silverman (eds.) 2001), 2001.
17. Schluesener, H. J., Sobel, R. A., Linington, C., and Weiner, H. L. A monoclonal antibody against a myelin oligodendrocyte glycoprotein induces relapses and demyelination in central nervous system autoimmune disease. J Immunol, 139: 4016-4021, 1987.

The invention claimed is:

1. An isolated human, xenogenic, or chimeric human-murine antibody or binding fragment thereof, which is capable of binding specifically to tumor-associated antigen NY-ESO-1, comprising in its variable heavy chain region the complementarity determining regions CDR1 of SEQ ID NO: 5, CDR2 of SEQ ID NO: 6, and CDR3 of SEQ ID NO: 7 and in its variable light chain region the complementarity determining regions CDR1 of SEQ ID NO: 8, CDR2 of SEQ ID NO: 9, and CDR3 of SEQ ID NO: 10.

2. The antibody or binding fragment of claim 1, which binds to an epitope defined by an amino acid sequence set forth in SEQ ID NO: 11.

3. The binding fragment of claim 1, selected from the group consisting of a single chain Fv fragment (scFv), a F(ab') fragment, a F(ab) fragment, and an F(ab')$_2$ fragment.

4. The antibody or binding fragment of claim 1, wherein the antibody or binding fragment comprises a variable heavy chain region comprising the amino acid sequence of SEQ ID NO: 2 or a variable light chain region comprising the amino acid sequence of SEQ ID NO: 4.

5. The antibody or binding fragment of claim 1, having a binding affinity of at least about $10^{-9}$M.

6. An antibody or a binding fragment thereof encoded by a polynucleotide encoding the variable heavy chain region and the variable light chain region of the antibody or binding fragment of claim 1.

7. The antibody or binding fragment of claim 1, which is detectably labeled.

8. The antibody or binding fragment of claim 7, wherein the detectable label is selected from the group consisting of an enzyme, a radioisotope, a fluorophore and a heavy metal.

9. The antibody or binding fragment of claim 1, which is attached to a drug.

10. A composition comprising the antibody or binding fragment of claim 1.

11. The composition of claim 10, which is a pharmaceutical composition and further comprises a pharmaceutically acceptable carrier.

12. The pharmaceutical composition of claim 11 further comprising an additional agent useful for treating tumors.

13. A diagnostic composition comprising the antibody or binding fragment of claim 1.

14. A kit for the diagnosis of a tumor, said kit comprising the antibody or binding fragment of claim 1.

* * * * *

UNITED STATES PATENT AND TRADEMARK OFFICE
CERTIFICATE OF CORRECTION

PATENT NO. : 8,519,106 B2  Page 1 of 1
APPLICATION NO. : 12/530764
DATED : August 27, 2013
INVENTOR(S) : Esslinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this

Fifteenth Day of September, 2015

Michelle K. Lee
*Director of the United States Patent and Trademark Office*